United States Patent
Satoh

(10) Patent No.: US 6,259,507 B1
(45) Date of Patent: Jul. 10, 2001

(54) RADIATION IMAGE READ-OUT APPARATUS

(75) Inventor: Kimihiko Satoh, Kaisei-machi (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 0 days.

(21) Appl. No.: 09/664,441

(22) Filed: Sep. 18, 2000

(30) Foreign Application Priority Data

Sep. 17, 1999 (JP) .................................................. 11-264216

(51) Int. Cl.[7] .......................... G03B 27/52; G03B 27/58; G01N 23/04; A61B 6/00

(52) U.S. Cl. .............................. 355/41; 355/43; 355/47; 355/49; 355/57; 355/65; 250/580; 250/581; 250/582; 250/586; 250/587

(58) Field of Search .................................. 355/41, 43, 47, 355/49, 57, 65; 250/580, 582, 581, 586, 587

(56) References Cited

U.S. PATENT DOCUMENTS

| | | | |
|---|---|---|---|
| 5,151,596 | * | 9/1992 | Saotome ............................ 350/327.2 |
| 5,446,292 | * | 8/1995 | Kohda ................................ 250/585 |
| 5,550,385 | * | 8/1996 | Nanami et al. ...................... 250/584 |
| 5,712,890 | * | 1/1998 | Spivey et al. ......................... 378/37 |
| 5,832,055 | * | 11/1998 | Dewaele ............................... 378/62 |

* cited by examiner

Primary Examiner—Russell Adams
Assistant Examiner—Khaled Brown
(74) Attorney, Agent, or Firm—Sughrue, Mion, Zinn, Macpeak & Seas, PLLC

(57) ABSTRACT

A stimulable phosphor sheet, on which a radiation image has been stored, is scanned with stimulating rays in a main scanning direction and moved in a sub-scanning direction, which is approximately normal to the main scanning direction. A read-out device photoelectrically detects the light, which is emitted by the stimulable phosphor sheet when the stimulable phosphor sheet is scanned with the stimulating rays in the main scanning direction, to obtain an image signal representing the radiation image. A light guiding mirror for reflecting the emitted light toward the read-out device is located to extend in the main scanning direction at a position in the vicinity of a position on the stimulable phosphor sheet, which position is scanned with the stimulating rays in the main scanning direction. The light guiding mirror is supported by a support member, which is formed from a metallic material and is electrically isolated from a ground, or which is formed from an electrical insulating material.

10 Claims, 3 Drawing Sheets

RADIATION IMAGE READ-OUT APPARATUS

BACKGROUND OF THE INVENTION

1. Field of the Invention

This invention relates to a radiation image read-out apparatus, wherein a stimulable phosphor sheet, on which a radiation image has been stored, is exposed to stimulating rays, and an image signal representing the radiation image is detected from the stimulable phosphor sheet.

2. Description of the Related Art

It has been proposed to use stimulable phosphors in radiation image recording and reproducing systems. Specifically, a radiation image of an object, such as a human body, is recorded on a sheet provided with a layer of the stimulable phosphor (hereinafter referred to as a stimulable phosphor sheet). The stimulable phosphor sheet, on which the radiation image has been stored, is then exposed to stimulating rays, such as a laser beam, which cause the stimulable phosphor sheet to emit light in proportion to the amount of energy stored thereon during its exposure to the radiation. The light emitted by the stimulable phosphor sheet, upon stimulation thereof, is photoelectrically detected with photoelectric read-out means, such as a photomultiplier, and converted into an electric image signal. The image signal is then processed and used for the reproduction of the radiation image of the object as a visible image on a recording material.

In the radiation image recording and reproducing systems described above, the light is emitted in a scattering state from the stimulable phosphor sheet. Therefore, a light guide member and a light guiding mirror are located in the vicinity of the position that is exposed to the stimulating rays. The light emitted in the scattering state from the stimulable phosphor sheet is reflected by the light guiding mirror toward the light guide member. In this manner, the efficiency, with which the emitted light is collected, is enhanced.

The light guiding mirror described above is supported by support means, which is formed from a metal. The support means is secured by screws, or the like, to a frame within a radiation image read-out apparatus. Therefore, the support means is in a grounded state (i.e., in the state in which the support means is electrically connected with a ground). In cases where the radiation image is read out from the stimulable phosphor sheet having been charged electrostatically, lines of electric force concentrate upon the support means, and dust clinging to the stimulable phosphor sheet clings to the light guiding mirror by electrostatic adsorption. If the dust clings to the light guiding mirror in this manner, the stimulating rays will be eclipsed by the dust. In such cases, since the stimulable phosphor sheet is also scanned with the stimulating rays in a sub-scanning direction, streak-like nonuniformity in image density occurs in the sub-scanning direction. Also, the light guiding mirror is formed with, for example, a technique, wherein a dichroic coating layer is formed on a glass substrate. Therefore, the light guiding mirror is adhered to the support means with an adhesive agent. In such cases, if the adhesive agent protrudes from the area of adhesion of the light guiding mirror and dust clings to the protruding adhesive agent, it will become difficult to remove the dust.

SUMMARY OF THE INVENTION

The primary object of the present invention is to provide a radiation image read-out apparatus, wherein dust is capable of being prevented from clinging to a light guiding mirror.

Another object of the present invention is to provide a radiation image read-out apparatus, wherein dust is capable of being prevented from clinging to a light guiding mirror, and a cost of the radiation image read-out apparatus is capable of being kept low.

The present invention provides a first radiation image read-out apparatus, comprising:

i) main scanning means for scanning a stimulable phosphor sheet, on which a radiation image has been stored, with stimulating rays in a main scanning direction, the stimulating rays causing the stimulable phosphor sheet to emit light in proportion to an amount of energy stored thereon during its exposure to radiation, ii) sub-scanning means for scanning the stimulable phosphor sheet in a sub-scanning direction, which is approximately normal to the main scanning direction, iii) read-out means for photoelectrically detecting the light, which is emitted by the stimulable phosphor sheet when the stimulable phosphor sheet is scanned with the stimulating rays in the main scanning direction, and obtaining an image signal representing the radiation image, iv) a light guiding mirror for reflecting the emitted light toward the read-out means, the light guiding mirror being located to extend in the main scanning direction at a position in the vicinity of a position on the stimulable phosphor sheet, which position is scanned with the stimulating rays in the main scanning direction, and v) support means for supporting the light guiding mirror, wherein the support means is formed from a metallic material and is electrically isolated from a ground.

In the first radiation image read-out apparatus in accordance with the present invention, the support means is electrically isolated from the ground. Specifically, the support means is in the state in which the support means is not grounded.

In the first radiation image read-out apparatus in accordance with the present invention, the light guiding mirror should preferably be constituted of a film-shaped member.

The term "film-shaped member" as used herein means the member, which does not have rigidity and has flexibility.

Also, in the first radiation image read-out apparatus in accordance with the present invention, the light guiding mirror should preferably be constituted of a filter, which absorbs the stimulating rays and has been subjected to mirror surface processing.

In the first radiation image read-out apparatus in accordance with the present invention, wherein the light guiding mirror is constituted of the film-shaped member, the support means should preferably be means for engaging with upper and lower ends of the light guiding mirror, such that the light guiding mirror is curved in a concave form.

The term "upper and lower ends of a light guiding mirror" as used herein means the two longitudinal side regions of the light guiding mirror, which extends in the main scanning direction. Therefore, with the support means, which is constituted to engage with the upper and lower ends of the light guiding mirror, the light guiding mirror is curved in the concave form, as viewed in a cross-section normal to the main scanning direction, and is thus curved into a cylindrical mirror-like shape.

The present invention also provides a second radiation image read-out apparatus, comprising:

i) main scanning means for scanning a stimulable phosphor sheet, on which a radiation image has been stored, with stimulating rays in a main scanning direction, the stimulating rays causing the stimulable phosphor sheet to emit light in proportion to an amount of energy stored thereon during its exposure to radiation, ii) sub-scanning means for scanning the stimulable phosphor sheet in a sub-scanning direction, which is approximately normal to the main scanning direction, iii) read-out means for photoelectrically detecting the light, which is emitted by the stimulable phosphor sheet when the stimulable phosphor sheet is scanned with the stimulating rays in the main scanning direction, and obtaining an image signal representing the radiation image, iv) a light guiding mirror for reflecting the emitted light toward the read-out means, the light guiding mirror being located to extend in the main scanning direction at a position in the vicinity of a position on the stimulable phosphor sheet, which position is scanned with the stimulating rays in the main scanning direction, and v) support means for supporting the light guiding mirror, wherein the support means is formed from an electrical insulating material.

As the electrical insulating material, a material having an electrical resistivity of at least $1 \times 10^2$ $\Omega$m may be employed. Examples of the electrical insulating materials include resins, rubber, and ceramic materials. As the resins, antistatic grades of resins may be employed. The antistatic grades of resins are the resins having an electrical resistivity of at least $1 \times 10^2$ $\Omega$m may be employed.

In the second radiation image read-out apparatus in accordance with the present invention, the light guiding mirror should preferably be constituted of a film-shaped member.

The term "film-shaped member" as used herein means the member, which does not have rigidity and has flexibility.

Also, in the second radiation image read-out apparatus in accordance with the present invention, the light guiding mirror should preferably be constituted of a filter, which absorbs the stimulating rays and has been subjected to mirror surface processing.

In the second radiation image read-out apparatus in accordance with the present invention, wherein the light guiding mirror is constituted of the film-shaped member, the support means should preferably be means for engaging with upper and lower ends of the light guiding mirror, such that the light guiding mirror is curved in a concave form.

The term "upper and lower ends of a light guiding mirror" as used herein means the two longitudinal side regions of the light guiding mirror, which extends in the main scanning direction. Therefore, with the support means, which is constituted to engage with the upper and lower ends of the light guiding mirror, the light guiding mirror is curved in the concave form, as viewed in a cross-section normal to the main scanning direction, and is thus curved into a cylindrical mirror-like shape.

The present invention further provides a third radiation image read-out apparatus, comprising:

i) main scanning means for scanning a stimulable phosphor sheet, on which a radiation image has been stored, with stimulating rays in a main scanning direction, the stimulating rays causing the stimulable phosphor sheet to emit light in proportion to an amount of energy stored thereon during its exposure to radiation, ii) sub-scanning means for scanning the stimulable phosphor sheet in a sub-scanning direction, which is approximately normal to the main scanning direction, iii) read-out means for photoelectrically detecting the light, which is emitted by the stimulable phosphor sheet when the stimulable phosphor sheet is scanned with the stimulating rays in the main scanning direction, and obtaining an image signal representing the radiation image, and iv) a light guiding mirror for reflecting the emitted light toward the read-out means, the light guiding mirror being located to extend in the main scanning direction at a position in the vicinity of a position on the stimulable phosphor sheet, which position is scanned with the stimulating rays in the main scanning direction, wherein the light guiding mirror is formed by performing mirror surface processing on a metallic material and is electrically isolated from a ground.

In the third radiation image read-out apparatus in accordance with the present invention, a mirror surface of the light guiding mirror should preferably be provided with a filter, which absorbs the stimulating rays.

With the first radiation image read-out apparatus in accordance with the present invention, the support means for supporting the light guiding mirror is formed from the metallic material and is electrically isolated from the ground. Also, with the second radiation image read-out apparatus in accordance with the present invention, the support means for supporting the light guiding mirror is formed from the electrical insulating material. Further, with the third radiation image read-out apparatus in accordance with the present invention, the light guiding mirror itself is formed by performing mirror surface processing on the metallic material and is electrically isolated from the ground. Therefore, with the first, second, and third radiation image read-out apparatuses in accordance with the present invention, even if the stimulable phosphor sheet is electrostatically charged when the radiation image is read out from the stimulable phosphor sheet, lines of electric force will not concentrate upon the support means. Accordingly, the problems do not occur in that dust clinging to the stimulable phosphor sheet clings to the light guiding mirror. As a result, an image signal is capable of being obtained, such that an image free from streak-like nonuniformity in image density due to dust can be reproduced from the image signal.

With the first and second radiation image read-out apparatuses in accordance with the present invention, wherein the light guiding mirror is constituted of the film-shaped member, processing of the light guiding mirror is capable of being performed easily. Therefore, the cost of the radiation image read-out apparatus is capable of being kept low.

With the first and second radiation image read-out apparatuses in accordance with the present invention, wherein the light guiding mirror is constituted of the filter, which absorbs the stimulating rays and has been subjected to the mirror surface processing, the stimulating rays are not reflected toward the stimulable phosphor sheet. Therefore, flare is capable of being prevented from occurring due to re-impingement of the stimulating rays upon the stimulable phosphor sheet.

With the first and second radiation image read-out apparatuses in accordance with the present invention, wherein the light guiding mirror is constituted of the film-shaped member, and the support means is means for engaging with the upper and lower ends of the light guiding mirror such that the light guiding mirror is curved in the concave form, the light guiding mirror is capable of being supported by the support means without any adhesive agent being used. Therefore, the problems do not occur in that an adhesive agent protrudes from the area of adhesion of the light guiding mirror and dust clings to the protruding adhesive agent. Also, ordinarily, processing of a light guiding mirror into a shape having a concave surface is not easy to perform and requires a high processing cost. However, with the first and second radiation image read-out apparatuses in accordance with the present invention, wherein the light guiding mirror is constituted of the film-shaped member, and the support means is means for engaging with the upper and lower ends of the light guiding mirror such that the light guiding mirror is curved in the concave form, the concave reflecting surface is capable of being formed easily. Therefore, the processing cost for the light guiding mirror and consequently the cost of the radiation image read-out apparatus are capable of being kept low.

DESCRIPTION OF THE PREFERRED EMBODIMENTS

The present invention will hereinbelow be described in further detail with reference to the accompanying drawings.

Figure 1:
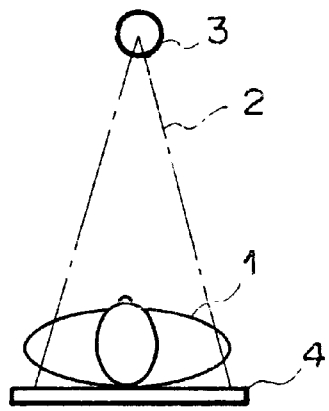
FIG. 1 is a schematic view showing a radiation image recording apparatus.

FIG. 1 is a schematic view showing a radiation image recording apparatus. As illustrated in FIG. 1, a stimulable phosphor sheet 4 is located at a position for image recording, and a radiation source 3 is operated to produce radiation 2. The radiation 2 is irradiated to an object 1. The radiation 2, which carries image information of the object 1, is irradiated to the stimulable phosphor sheet 4, and a radiation image of the object 1 is thereby stored on the stimulable phosphor sheet 4.

Figure 2:
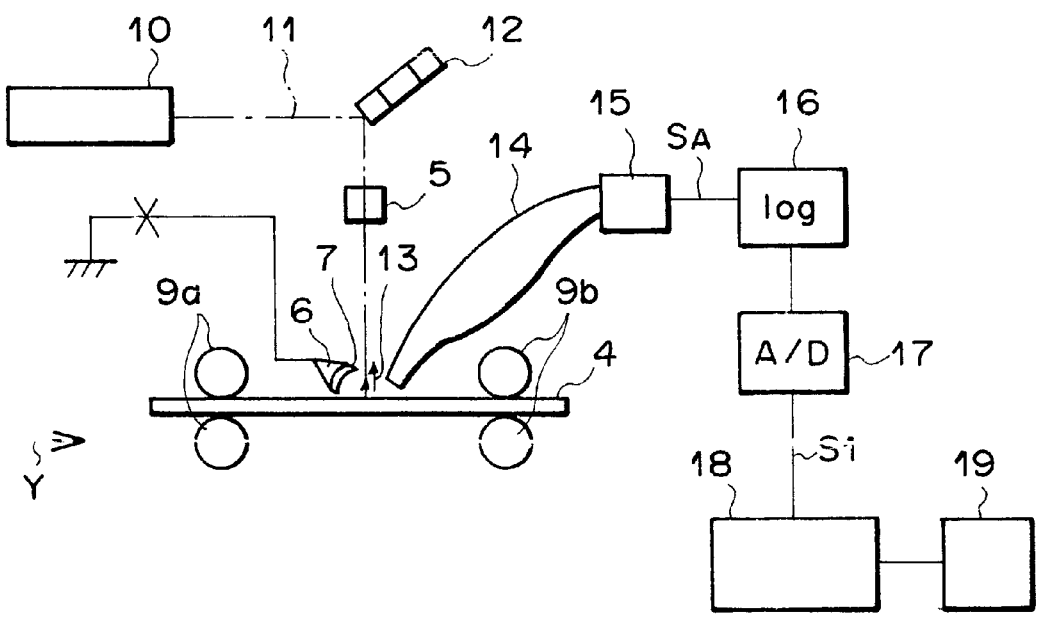
FIG. 2 is an explanatory view showing an embodiment of the radiation image read-out apparatus in accordance with the present invention.

Thereafter, as illustrated in FIG. 2, with an embodiment of the radiation image read-out apparatus in accordance with the present invention, the radiation image is read out from the stimulable phosphor sheet 4, on which the radiation image has been stored, and an image signal representing the radiation image is thereby obtained.

With reference to FIG. 2, the stimulable phosphor sheet 4 is conveyed by conveying rollers 9a, 9a nd conveying rollers 9b, 9b, which are rotated by motors (not shown). The stimulable phosphor sheet 4 is thus conveyed in the sub-scanning direction indicated by the arrow Y. A laser beam source 10, which produces a laser beam 11 acting as the stimulating rays, and a rotating polygon mirror 12, which is rotated by a motor (not shown), are located above the stimulable phosphor sheet 4, which is conveyed by the conveying rollers 9a, 9a and the conveying rollers 9b, 9b. The rotating polygon mirror 12 reflects and deflects the laser beam 11 and causes the laser beam 11 to scan on the stimulable phosphor sheet 4 in the main scanning direction. The laser beam 11 causes the stimulable phosphor sheet 4 to emit light 13 in proportion to the amount of energy stored thereon during its exposure to the radiation 2. Also, a light guide member 14 is located close to the conveyance path of the stimulable phosphor sheet 4 and above the position on the stimulable phosphor sheet 4, which position is scanned with the laser beam 11. The light guide member 14 guides the light 13, which is emitted by the stimulable phosphor sheet 4 when the stimulable phosphor sheet 4 is scanned with the laser beam 11. Further, a light guiding mirror 7 is located in the vicinity of the light guide member 14. The light guiding mirror 7 reflects the light 13, which is emitted in a scattering state from the stimulable phosphor sheet 4, toward the light guide member 14. The light guiding mirror 7 is supported by a mirror mount 6. The light guide member 14 is connected to a photomultiplier 15 for photoelectrically detecting the emitted light 13. The photomultiplier 15 is connected to a logarithmic amplifier 16. The logarithmic amplifier 16 is connected to an analog-to-digital converter 17. The analog-to-digital converter 17 is connected to storage means 18. The storage means 18 is connected to image processing means 19.

Figure 3:
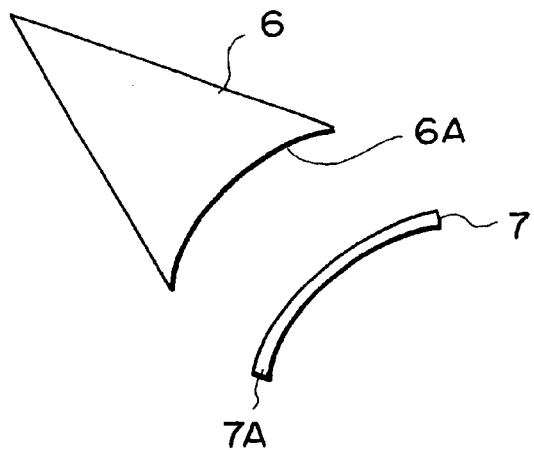
FIG. 3 is an explanatory view showing a mirror mount and a light guiding mirror.

The mirror mount 6 is formed from a metallic material. As illustrated in FIG. 3, the mirror mount 6 is provided with a concave region 6A. The light guiding mirror 7, which is formed from a flexible material, such as a film, is adhered with an adhesive agent to the concave region 6A of the mirror mount 6. The light guiding mirror 7 is constituted of a filter material 7A, which is capable of absorbing light having wavelengths falling within the wavelength range of the laser beam 11. One surface of the filter material 7A, i.e. the surface to be adhered to the concave region 6A of the mirror mount 6, has been subjected to mirror surface processing, such as aluminum vacuum evaporation processing.

Figure 4:
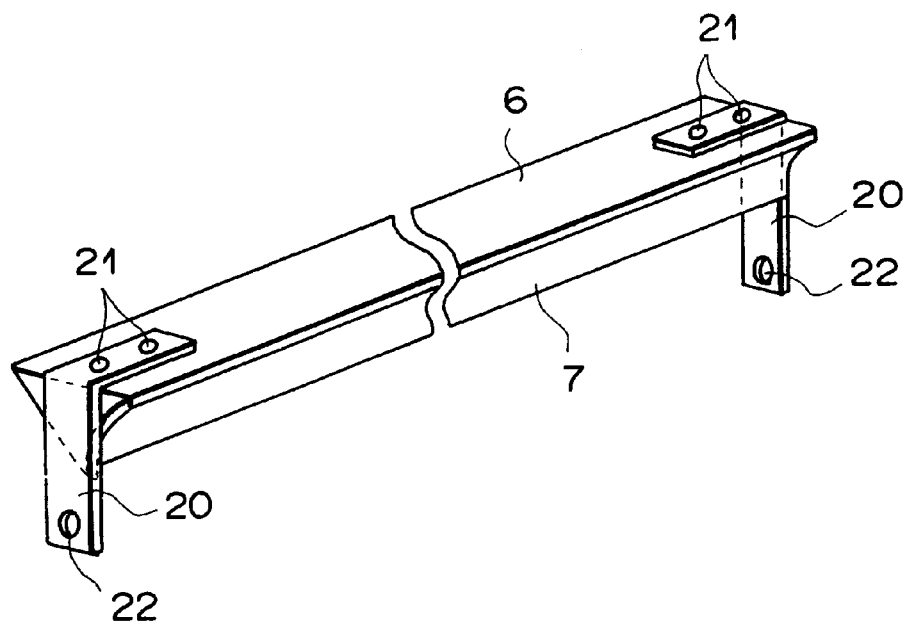
FIG. 4 is an explanatory view showing how the mirror mount is secured to the radiation image read-out apparatus.

FIG. 4 is an explanatory view showing how the mirror mount 6 is secured to the radiation image read-out apparatus. As illustrated in FIG. 4, brackets 20, 20, which are formed from an electrical insulating material, such as a resin, rubber, or a ceramic material, are secured by screws 21, 21, . . . to the mirror mount 6. The brackets 20, 20 are secured to a frame (not shown) of the radiation image read-out apparatus and with screws inserted through screw holes 22, 22. In this manner, the mirror mount 6 is secured via the brackets 20, 20, which are formed from the electrical insulating material, to the radiation image read-out apparatus. Therefore, as illustrated in FIG. 2, the mirror mount 6 is in the state in which the mirror mount 6 is electrically isolated from the ground. (In FIG. 2, the electrical isolation is indicated by the "x" mark.)

How this embodiment of the radiation image read-out apparatus in accordance with the present invention operates will be described hereinbelow.

The stimulable phosphor sheet 4, on which the radiation image of the object 1 has been stored, is set between the conveying rollers 9a, 9a. The stimulable phosphor sheet 4, which has been set between the conveying rollers 9a, 9a, is conveyed by the conveying rollers 9a, 9a and conveying rollers 9b, 9b in the sub-scanning direction indicated by the arrow Y. The laser beam 11, which has been produced by the laser beam source 10, is reflected and deflected by the rotating polygon mirror 12, which is rotated quickly by the motor (not shown). The laser beam 11, which has thus been reflected and deflected by the rotating polygon mirror 12, impinges upon the stimulable phosphor sheet 4. The laser beam 11 is thus caused to scan on the stimulable phosphor sheet 4 in the main scanning direction, which is approximately normal to the sub-scanning direction indicated by the arrow Y, and which is normal to the plane of the sheet of FIG. 1. When the stimulable phosphor sheet 4 is conveyed to the position, which is exposed to the laser beam 11, the portion of the stimulable phosphor sheet 4, which portion is exposed to the laser beam 11, emits the light 13 in proportion to the amount of energy stored thereon during its exposure to the radiation 2. The light 13 is thus emitted in the scattering state from the surface of the stimulable phosphor sheet 4. However, the emitted light 13, which travels toward the light guiding mirror 7, is reflected by the light guiding mirror 7 and guided toward the light guide member 14. The light guiding mirror 7 is capable of absorbing light having wavelengths falling within the wavelength range of the laser beam 11. Therefore, the laser beam 11 is not reflected by the light guiding mirror 7. Accordingly, flare can be prevented from occurring due to re-impingement of the laser beam 11 upon the stimulable phosphor sheet 4.

The emitted light 13 enters into the light guide member 14 from its light input end face. The emitted light 13, which has entered into the light guide member 14, is guided inside of the light guide member 14 through repeated total reflection, emanates from a light output end face of the light guide member 14, and is received by the photomultiplier 15. The intensity of the emitted light 13, which carries the radiation image information, is converted by the photomultiplier 15 into an electric image signal. In this manner, an analog image signal SA is obtained from the photomultiplier 15.

The analog image signal SA having been obtained from the photomultiplier 15 is logarithmically amplified by the logarithmic amplifier 16 and is then fed into the analog-to-digital converter 17. The analog image signal SA is converted by the analog-to-digital converter 17 into a digital image signal S1. The digital image signal S1 is fed into and stored in the storage means 18. The digital image signal S1 is then read from the storage means 18 and fed into the image processing means 19. In the image processing means 19, predetermined image processing is performed on the digital image signal S1, and a processed image signal is thereby obtained. The processed image signal having been obtained from the image processing means 19 is fed into image reproducing means (not shown) and used for reproducing a visible radiation image. The image reproducing means may be display means, such as a cathode ray tube (CRT) display device, or may be a recording device for recording the image on photosensitive film through optical scanning.

If the stimulable phosphor sheet 4, on which the radiation image has been stored, is charged electrostatically, lines of electric force will concentrate upon a member formed from a metal, which member is electrically connected with the ground. Therefore, dust clinging to the stimulable phosphor sheet 4 will cling to the member by electrostatic adsorption. In particular, if the mirror mount 6 formed from the metallic material is electrically connected with the ground, dust will cling to the light guiding mirror 7. If the dust thus clings to the light guiding mirror 7, the stimulating rays will be eclipsed by the dust, and therefore streak-like nonuniformity in image density will occur in the sub-scanning direction in the obtained image. However, in this embodiment of the radiation image read-out apparatus in accordance with the present invention, the mirror mount 6 is secured to the radiation image read-out apparatus via the brackets 20, 20, which are formed from an electrical insulating material. Therefore, in this embodiment, the mirror mount 6 is electrically isolated from the ground. Accordingly, even if the stimulable phosphor sheet 4 is charged electrostatically, lines of electric force will not concentrate upon the mirror mount 6, and dust clinging to the stimulable phosphor sheet 4 will not cling to the light guiding mirror 7. As a result, an image signal is capable of being obtained, such that an image free from streak-like nonuniformity in image density due to dust can be reproduced from the image signal.

Figure 5:
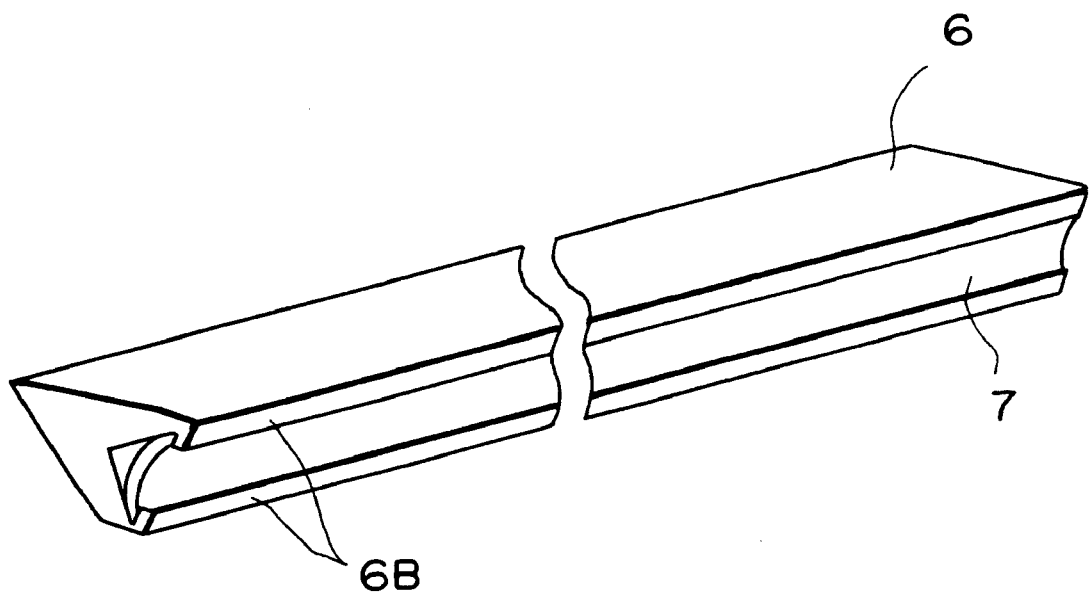
FIG. 5 is a schematic view showing a different example of a mirror mount.

In the embodiment described above, the light guiding mirror 7 is adhered to the mirror mount 6 with the adhesive agent. Alternatively, as illustrated in FIG. 5, the mirror mount 6 may be provided with engagement regions 6B, 6B for engaging with the longitudinal side regions of the light guiding mirror 7, and the light guiding mirror 7 may be fitted to the engagement regions 6B, 6B such that the light guiding mirror 7 may be curved in the concave form. In cases where the light guiding mirror 7 is adhered to the mirror mount 6 with the adhesive agent as in the embodiment described above, if the adhesive agent protrudes from the area of adhesion of the light guiding mirror 7, the problems will occur in that dust clings to the protruding adhesive agent, and the dust clinging to the protruding adhesive agent cannot be removed easily. However, in cases where the light guiding mirror 7 is fitted to the mirror mount 6 in the manner shown in FIG. 5, since an adhesive agent need not be utilized, the problems do not occur in that an adhesive agent protrudes from the area of adhesion of the light guiding mirror 7 and dust clings to the protruding adhesive agent and cannot be removed easily. Also, ordinarily, processing of the surface of the mirror mount 6, to which the light guiding mirror 7 is to be secured, into a concave surface is not easy to perform and requires a high processing cost. However, in cases where the longitudinal side regions of the light guiding mirror 7 are engaged with the mirror mount 6 in the manner shown in FIG. 5, the concave reflecting surface is capable of being formed easily. Therefore, the processing cost for the light guiding mirror 7 and consequently the cost of the radiation image read-out apparatus are capable of being kept low.

Also, in the embodiment described above, the light guiding mirror 7 is secured to the concave region 6A of the mirror mount 6. Alternatively, the concave region 6A of the mirror mount 6 may be subjected to mirror surface processing, and the mirror mount 6 itself may be provided with the functions for the light guiding mirror. In such cases, it is necessary for the regions of the mirror mount 6 other than the concave region 6A to be subjected to blackening processing such that the other regions of the mirror mount 6 may not reflect light. Also, in such cases, the concave region 6A having been subjected to the mirror surface processing should preferably be provided with a filter, which is capable of absorbing light having wavelengths falling within the wavelength range of the laser beam 11. In cases where the concave region 6A having been subjected to the mirror surface processing is provided with the filter, the mirror mount 6 may be provided with the engagement regions 6B, 6B as illustrated in FIG. 5, and the filter may be engaged with the engagement regions 6B, 6B. In such cases, an adhesive agent need not be utilized, and the filter can be easily fitted to the mirror mount 6.

Further, in the embodiment described above, the mirror mount 6 is formed from the metallic material. Alternatively, the mirror mount 6 may be formed from an electrical insulating material. As the electrical insulating material, a material having an electrical resistivity of at least $1 \times 10^2$ $\Omega$m may be employed. Specifically, resins, rubber, ceramic materials, and the like, may be employed as the electrical insulating material. In cases where the resins are employed, antistatic grades of resins, which have an electrical resistivity of at least $1 \times 10^2$ $\Omega$m may be employed. In such cases, the mirror mount 6 may be connected with the ground. Therefore, as the brackets 20, 20 for securing the mirror mount 6 to the radiation image read-out apparatus, brackets formed from a metal may be utilized. In cases where the mirror mount 6 is formed from the electrical insulating material, the mirror mount 6 is capable of being set in the state in which the mirror mount 6 is electrically isolated from the ground. Therefore, in such cases, even if the stimulable phosphor sheet 4 is charged electrostatically, the problems do not occur in that dust clinging to the stimulable phosphor sheet 4 clings to the light guiding mirror 7 by electrostatic adsorption. Accordingly, an image signal is capable of being obtained, such that an image free from streak-like nonuniformity in image density due to dust can be reproduced from the image signal.

In cases where the mirror mount 6 is formed from the electrical insulating material, it is necessary for the light guiding mirror 7 to be the one which has been subjected to the mirror surface processing, such as aluminum vacuum evaporation processing.

In the embodiment described above, the light guiding mirror 7 is constituted of the flexible material, such as a film. Alternatively, the light guiding mirror 7 may be constituted of a material having rigidity, such as glass.

In addition, all of the contents of Japanese Patent Application No. 11(1999)-264216 are incorporated into this specification by reference.

What is claimed is:

1. A radiation image read-out apparatus, comprising:
   i) main scanning means for scanning a stimulable phosphor sheet, on which a radiation image has been stored, with stimulating rays in a main scanning direction, the stimulating rays causing the stimulable phosphor sheet to emit light in proportion to an amount of energy stored thereon during its exposure to radiation,
   ii) sub-scanning means for scanning the stimulable phosphor sheet in a sub-scanning direction, which is approximately normal to the main scanning direction,
   iii) read-out means for photoelectrically detecting the light, which is emitted by the stimulable phosphor sheet when the stimulable phosphor sheet is scanned with the stimulating rays in the main scanning direction, and obtaining an image signal representing the radiation image,
   iv) a light guiding mirror for reflecting the emitted light toward the read-out means, the light guiding mirror being located to extend in the main scanning direction at a position in the vicinity of a position on the stimulable phosphor sheet, which position is scanned with the stimulating rays in the main scanning direction, and
   v) support means for supporting the light guiding mirror, wherein the support means is formed from a metallic material and is electrically isolated from a ground.

2. An apparatus as defined in claim 1 wherein the light guiding mirror is constituted of a film-shaped member.

3. An apparatus as defined in claim 2 wherein the light guiding mirror is constituted of a filter, which absorbs the stimulating rays and has been subjected to mirror surface processing.

4. An apparatus as defined in claim 2 or 3 wherein the support means is means for engaging with upper and lower ends of the light guiding mirror, such that the light guiding mirror is curved in a concave form.

5. A radiation image read-out apparatus, comprising:
   i) main scanning means for scanning a stimulable phosphor sheet, on which a radiation image has been stored, with stimulating rays in a main scanning direction, the stimulating rays causing the stimulable phosphor sheet to emit light in proportion to an amount of energy stored thereon during its exposure to radiation,
   ii) sub-scanning means for scanning the stimulable phosphor sheet in a sub-scanning direction, which is approximately normal to the main scanning direction,
   iii) read-out means for photoelectrically detecting the light, which is emitted by the stimulable phosphor sheet when the stimulable phosphor sheet is scanned with the stimulating rays in the main scanning direction, and obtaining an image signal representing the radiation image,
   iv) a light guiding mirror for reflecting the emitted light toward the read-out means, the light guiding mirror being located to extend in the main scanning direction at a position in the vicinity of a position on the stimulable phosphor sheet, which position is scanned with the stimulating rays in the main scanning direction, and
   v) support means for supporting the light guiding mirror, wherein the support means is formed from an electrical insulating material.

6. An apparatus as defined in claim 5 wherein the light guiding mirror is constituted of a film-shaped member.

7. An apparatus as defined in claim 6 wherein the light guiding mirror is constituted of a filter, which absorbs the stimulating rays and has been subjected to mirror surface processing.

8. An apparatus as defined in claim 6 or 7 wherein the support means is means for engaging with upper and lower ends of the light guiding mirror, such that the light guiding mirror is curved in a concave form.

9. A radiation image read-out apparatus, comprising:
   i) main scanning means for scanning a stimulable phosphor sheet, on which a radiation image has been stored, with stimulating rays in a main scanning direction, the stimulating rays causing the stimulable phosphor sheet to emit light in proportion to an amount of energy stored thereon during its exposure to radiation,
   ii) sub-scanning means for scanning the stimulable phosphor sheet in a sub-scanning direction, which is approximately normal to the main scanning direction,
   iii) read-out means for photoelectrically detecting the light, which is emitted by the stimulable phosphor sheet when the stimulable phosphor sheet is scanned with the stimulating rays in the main scanning direction, and obtaining an image signal representing the radiation image, and
   iv) a light guiding mirror for reflecting the emitted light toward the read-out means, the light guiding mirror being located to extend in the main scanning direction at a position in the vicinity of a position on the stimulable phosphor sheet, which position is scanned with the stimulating rays in the main scanning direction,
   wherein the light guiding mirror is formed by performing mirror surface processing on a metallic material and is electrically isolated from a ground.

10. An apparatus as defined in claim 9 wherein a mirror surface of the light guiding mirror is provided with a filter, which absorbs the stimulating rays.

* * * * *